(12) United States Patent
Bruder et al.

(10) Patent No.: US 6,859,512 B2
(45) Date of Patent: Feb. 22, 2005

(54) METHOD FOR COMPUTER TOMOGRAPHY AND COMPUTER TOMOGRAPHY DEVICE FOR CARRYING OUT THE METHOD

(75) Inventors: Herbert Bruder, Höchstadt (DE); Thomas Flohr, Uehlfeld (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/477,628
(22) PCT Filed: May 16, 2002
(86) PCT No.: PCT/DE02/01760
§ 371 (c)(1), (2), (4) Date: Nov. 14, 2003
(87) PCT Pub. No.: WO02/093489
PCT Pub. Date: Nov. 21, 2002

(65) Prior Publication Data
US 2004/0146137 A1 Jul. 29, 2004

(30) Foreign Application Priority Data
May 16, 2001 (DE) ......................................... 101 23 798

(51) Int. Cl.[7] .............................................. A61B 6/03
(52) U.S. Cl. ............................. 378/4; 378/19; 378/901
(58) Field of Search ........................... 378/4, 8, 15, 19, 378/901

(56) References Cited

U.S. PATENT DOCUMENTS

| | | | |
|---|---|---|---|
| 5,375,156 A | 12/1994 | Kuo-Petravic et al. | 378/9 |
| 5,708,691 A | 1/1998 | Zmora | 378/4 |
| 6,285,733 B1 | 9/2001 | Proksa et al. | 378/15 |
| 6,435,714 B1 | 8/2002 | Bruder | 378/196 |

FOREIGN PATENT DOCUMENTS

| | | |
|---|---|---|
| DE | 19502574 | 8/1996 |
| DE | 19936679 | 3/2001 |
| EP | 0990892 | 4/2000 |

OTHER PUBLICATIONS

Kopp, A.F. et al.: "Multislice Computed Tomography: Basic Principles and Clinical Applications", Electromedica 68(2000) No. 2, pp. 94 to 105.
Turbell, H. :Cone–Beam, "Reconstruction Using Filtered Backprojection", Dissertation No. 672, University of Linköping, Feb. 2001.
Turbell, H. : Cone–Beam, "Reconstruction Using Filtered Backprojection", Abstract Dissertation No. 672, University of Linköping, Feb. 23, 2001.
Rizo, P. et al.: "Comparison of Two Three–Dimensional X–Ray Cone–Beam–Reconstruction Algorithms with Circular Source Trajectories", in Journal of the Optical Society of America, vol. 8, No. 10, Oct. 1991, pp. 1639 to 1648.
Bruder, H. et al.: "Performance of approximate cone–beam reconstruction in multi–slice computed tomography": in Medical Imaging 2000. Image Processing, Proceedings of the SPIE vol. 3979(2000), pp. 541 to 553.

*Primary Examiner*—David V Bruce
(74) *Attorney, Agent, or Firm*—Harness, Dickey & Pierce, P.L.C.

(57) ABSTRACT

Cone-beam computed tomography method to scan an object using a multi-row detector system. The focal point is displaced on a focal path about the system axis, without any relative movement between the object to be examined and the focal point, in the direction of the system axis. The detector system supplies measuring data corresponding to the received radiation and the length of the focal path is at least the same as the length of a partial contour interval, the length of the interval being sufficient for completely reconstructing a CT image. Raw images are calculated from measuring data from a partial contour interval, the planes of the images thereof being inclined in relation to a central plane containing the focal path, and a plurality of raw images are collected to form a CT image.

47 Claims, 3 Drawing Sheets

METHOD FOR COMPUTER TOMOGRAPHY AND COMPUTER TOMOGRAPHY DEVICE FOR CARRYING OUT THE METHOD

This application is the national phase under 35 U.S.C. § 371 of PCT International Application No. PCT/DE02/01760 which has an International filing date of May 16, 2002, which designated the United States of America and which claims priority on German Patent Application number DE 101 23 798.7 filed May 16, 2001, the entire contents of which are hereby incorporated herein by reference.

FIELD OF THE INVENTION

The invention generally relates to a method for computed tomography (CT). Preferably, it relates to a CT method in which, in order to scan an object with the aid of a conical beam emanating from a focus and the aid of a detector system, having a plurality of rows of detector elements for detecting the beam, the focus is moved on a focal path about a system axis without relative movement between the object to be examined and the focus in the direction of the system axis. The detector system preferably supplies measured data corresponding to the received radiation. The length of the focal path is preferably at least equal to the length of a partial revolution interval whose length suffices for the complete reconstruction of a computed tomography (CT) image. The invention also generally relates to a computed tomography device for carrying out such a method.

BACKGROUND OF THE INVENTION

In known methods, a CT image is calculated in each case from the measured data supplied from the individual rows. The data inconsistencies caused by the so-called cone angle (that is to say the inclination, of the rays to the image plane) occurring as a consequence of the use of a conical beam can be neglected in this case as long as the number of rows is sufficiently low and does not exceed 4, for example. In the case of detector systems with a larger number of rows, for example 16 rows, however, substantial artifacts occur in the CT images that are reconstructed on the basis of the measured data supplied from the outer rows.

Methods of the Feldkamp type, in which a 3D Backprojection is carried out after a convolution in the data, may be a solution to this problem. However, such methods are substantially more complex than 2D reconstruction methods.

SUMMARY OF THE INVENTION

An object of an embodiment of the invention is to specify a method that at least reduces the artifacts caused by the use of a conical beam, doing so in a simple way. It is also an object of an embodiment of invention to specify a computed tomography device for carrying out such a method.

Accordingly, raw images, whose image planes are inclined relative to a central plane containing the focal path, are calculated from measured data originating from a partial revolution interval. These raw images, which can equally be CT images, are then combined to form a resulting CT image.

It thus becomes clear that in the case of the inventive method the image planes of the raw images are different from the image plane of the resulting CT image and are inclined with reference to the central plane in contrast to the image plane of the resulting CT image. The inclined image planes of the raw images ensure that the resulting CT image is calculated on the basis of CT images, specifically on the basis of the raw images, that contain no artifacts, or at least no substantial ones, determined by influences of the cone angle. The reason why such artifacts cannot occur in the raw images, or can do so only to a slight extent, is that, because of the inclined image planes of the raw images, rays that run in the image plane of the respective raw image are present for the reconstruction of the raw images, at least over a large part of the respective partial revolution interval.

Since the raw images thus contain no artifacts, or at least no substantial ones, determined by influences of the cone angle, the preconditions exist for it also to be possible to produce a resulting CT image, having few artifacts, with reference to a desired image plane by combining a plurality of raw images. On the other hand, the radiation dose fed to an object to be examined is used effectively since measured data originating from a plurality of rows of detector elements have some influence on the resulting CT image.

In accordance with a preferred embodiment of the invention, the raw images are combined to form a resulting CT image by weighting, the pixels of the raw images in each case contributing as source pixels to a corresponding target pixel of the resulting CT image, and the contribution of a source pixel to a target pixel being weighted as a function of a geometric reference variable. The result of this is that not only does the respectively resulting CT image have few artifacts with respect to the influences of the cone angle, but also no appreciable artifacts are produced by the combination of a plurality of raw images. In this case, the distance of the respective source pixel from the corresponding target pixel and/or the distance of the respective source pixel from the center of the corresponding partial revolution interval are/is taken into account as (a) geometric reference variable (s).

Alternatively, the combination of a plurality of raw images to form a resulting CT image can be performed by interpolation, that is to say the value of a pixel of the resulting CT image is determined by interpolation from the corresponding pixels of the raw images to be combined.

In the interest of a high image quality of the resulting CT image, it is expedient when raw images are calculated whose image plane intersect in a straight line, in particular in a tangent to the focal path.

In cases where the aim is to achieve a particularly high temporal resolution, it is expedient to calculate raw images from a single partial revolution interval. Otherwise, in accordance with a preferred variant of an embodiment of the invention, raw images are calculated with reference to a plurality of mutually overlapping partial revolution intervals. Further, raw images originating from different partial revolution intervals are superimposed to form the resulting CT image, since then an image quality increased once more is achieved in conjunction with good dose usage and low image noise.

For each row of detector elements, the measured data include per position of the focus and per detector element, a measured value that is referred to below as a ray. As a consequence of the cone angle, the rays belonging to the different focal positions of a partial revolution interval lie not only not in a common plane, but also not even in a common surface. A particularly high image quality of the resulting CT images is therefore achieved when, in accordance with a preferred variant of an embodiment of the invention, the reconstruction of a raw image is performed on the basis of measured data that are selected from the measured data, supplied from the individual rows of detector elements, in such a way that the rays used for the reconstruction of the respective raw image fulfill a suitable error criterion with regard to their distance from the inclined image plane of the respective raw image.

It is ensured in this way that a raw image is respectively calculated on the basis of those rays that are situated in their totality most favorably relative to the image plane of the raw image. A suitable error criterion is, for example, the minimum quadratic mean value of the distance, measured in the z direction, of all the rays, used for the reconstruction of the respective raw image, from the inclined image plane of the respective raw image.

According to variants of embodiments of the invention, the layer thickness, also denoted as the reconstruction layer thickness, of the resulting CT image is set via the number of raw images produced per partial revolution interval, or the number of raw images incorporated into the combination, and/or by weighting the raw images incorporated into the combination.

In accordance with a variant of an embodiment of the invention, a raw image whose image plane is the central plane is calculated and incorporated into the combination. Since it is to be expected that artifacts caused by the cone angle are virtually not present in the case of such an image, the incorporation of such a raw image into the combination has a favorable effect on the image quality of the resulting CT image.

In accordance with embodiments of the invention, it is possible to produce, as the resulting CT image, an axial image, that is to say an image whose image plane corresponds to the central plane, a resulting CT image with an image plane inclined to the central plane, or a resulting CT image with reference to a non-planar section of the object.

The part of the object relating to a CT device may further be achieved by the CT device of an embodiment of the present invention, and reference is made in respect of their advantages to the above explanations of the method according to an embodiment of the invention.

BRIEF DESCRIPTION OF THE DRAWINGS

The present invention will become more fully understood from the detailed description of preferred embodiments given hereinbelow and the accompanying drawings, which are given by way of illustration only and thus are not limitative of the present invention, and wherein.

DETAILED DESCRIPTION OF THE PREFERRED EMBODIMENTS

Figure 1:
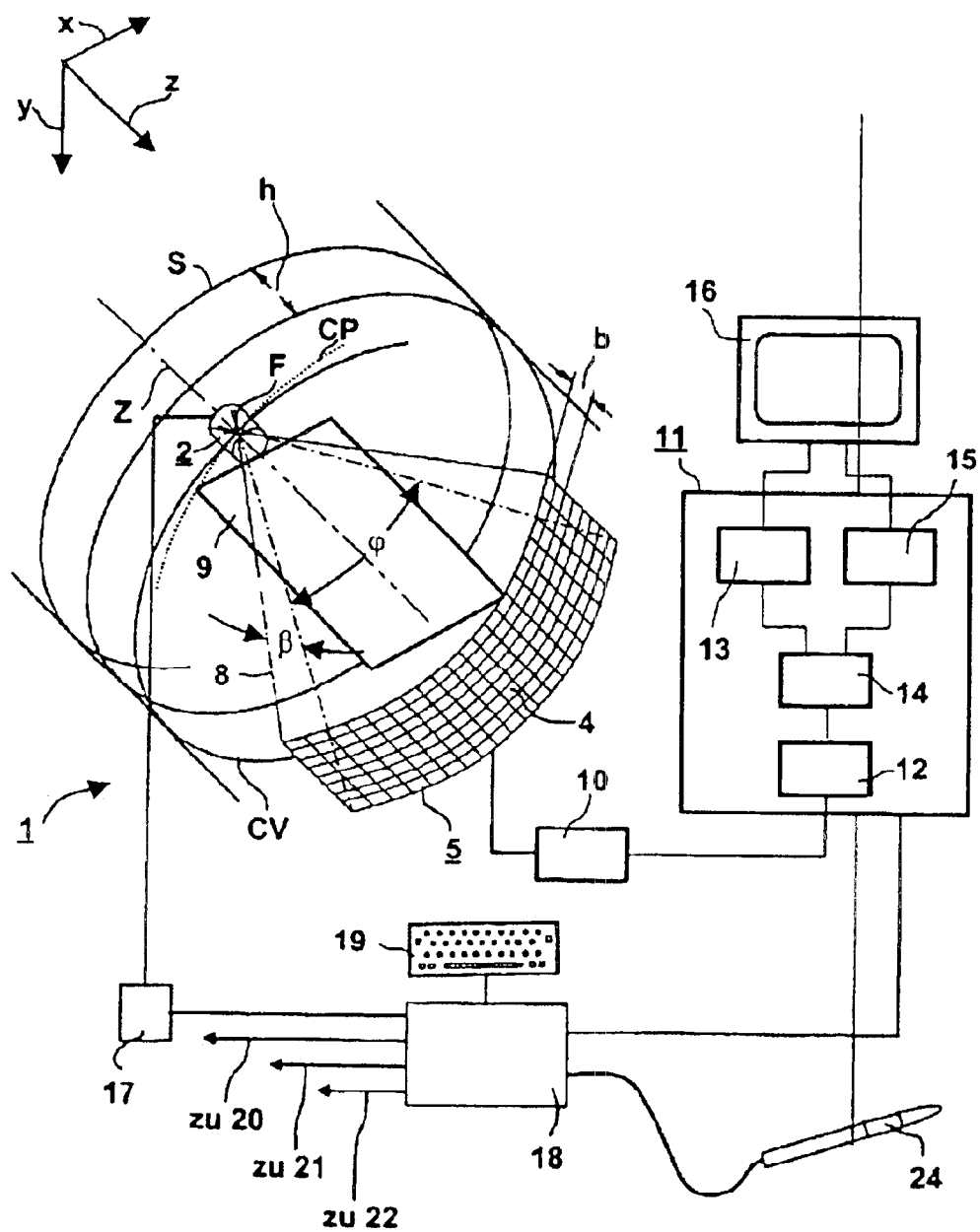
FIG. 1 shows an illustration, in part perspective and in part as a block diagram, of a CT device according to an embodiment of the invention having a plurality of rows of detector elements.
Figure 2:
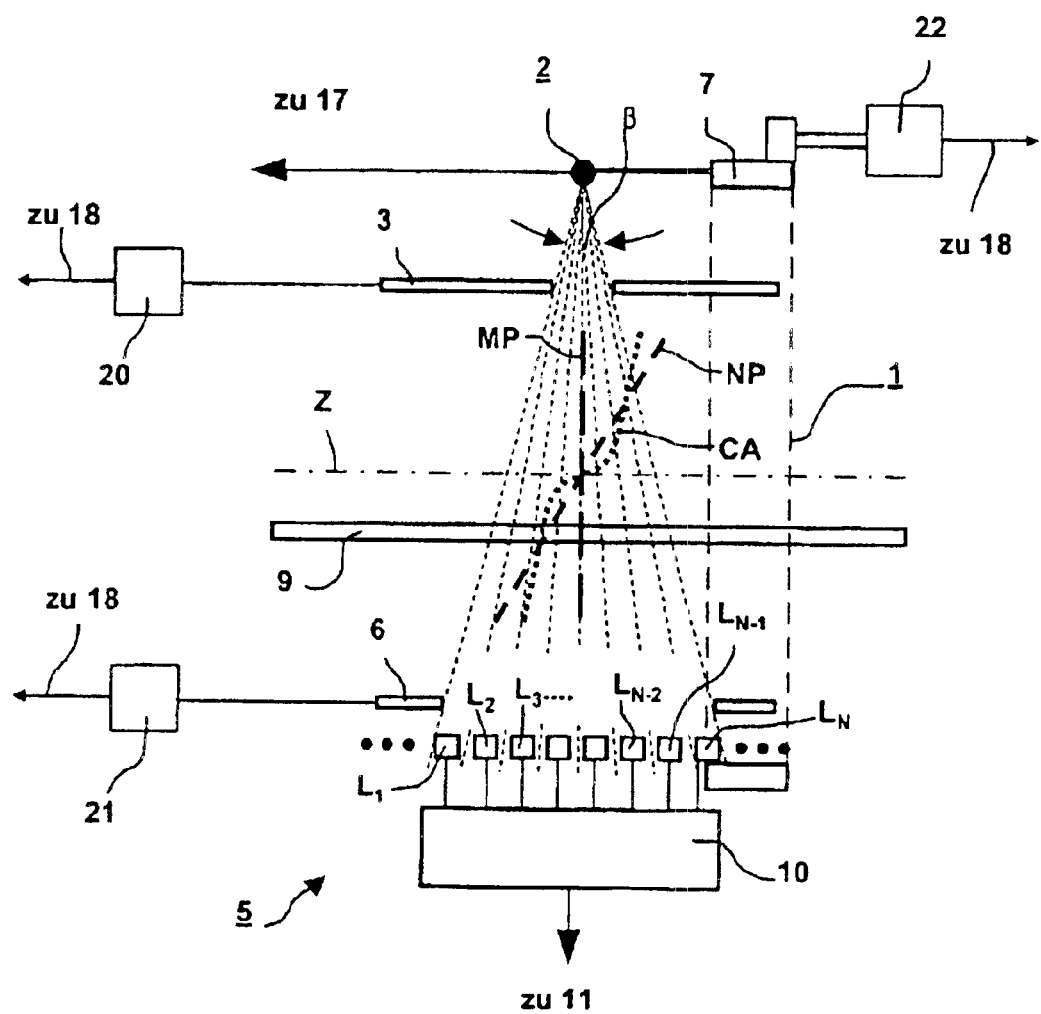
FIG. 2 shows a longitudinal section through the device in accordance with FIG. 1 in a first operating mode.

FIGS. 1 and 2 illustrate a CT device of the third generation which is suitable for carrying out the method according to an embodiment of the invention. Its measuring arrangement, designated overall by 1, has an X-ray source, designated overall by 2, with a radiation aperture 3 (FIG. 2) placed in front of it and close to the source, and a detector system 5, constructed as a two-dimensional array of a plurality of rows and columns of detector elements—one of these is designated by 4 in FIG. 1—and with a radiation aperture 6 (FIG. 2) placed in front of it and close to the detector. In FIG. 1, for reasons of clarity, only eight rows of detector elements 4 are illustrated, but the detector system 5 has further rows of detector elements 4, which is indicated by dots in FIG. 2.

The X-ray source 2 with the radiation aperture 3, on the one hand, and the detector system 5 with the radiation aperture 6, on the other hand, are fitted opposite each other on a rotary frame 7, in the manner which can be seen in FIG. 2. They are fitted in such a way that a pyramidal X-ray beam which, during the operation of the CT device, originates from the X-ray source 2 and is collimated by the adjustable radiation aperture 3 and whose edge rays are designated by 8, strikes the detector system 5. In the process, the radiation aperture 6 is set to correspond to the cross section, set by way of the radiation aperture 3, of the X-ray beam in such a way that only that area of the detector system 5 which can be struck directly by the X-ray beam is exposed.

In the operating mode illustrated in FIGS. 1 and 2, this is eight rows of detector elements 4, which are referred to as active rows below. The further rows indicated by dots are covered by the radiation aperture 6 and are therefore inactive. Each row of detector elements 4 has a number K of detector elements, k=1 to K being the so-called channel index. The active rows $L_n$ of detector elements 4 are designated by $L_1$ to $L_N$ in FIG. 2, n=1 to N being the row index.

The X-ray beam has the cone angle $\beta$, plotted in FIG. 2, which is the opening angle of the X-ray beam in a plane containing the system axis Z and the focus F. The fan angle $\phi$ of the X-ray beam, which is the opening angle of the X-ray beam in a plane lying at right angles to the system axis Z and containing the focus F, is plotted in FIGS. 1 and 3.

The rotary frame 7 can be set rotating about a system axis designated by Z by way of a drive device 22. The system axis Z runs parallel to the z axis of a three-dimensional rectangular coordinate system illustrated in FIG. 1.

The columns of the detector system 5 likewise run in the direction of the z axis, while the rows, whose width b is measured in the direction of the z axis and is 1 mm, for example, run transversely with respect to the system axis Z and the z axis.

In order to bring, an object to be examined, for example a patient, into the beam path of the X-ray beam, a bearing device 9 is provided, which can be displaced parallel to the system axis Z, that is to say in the direction of the z axis. This is done specifically in such a way that there is synchronization between the rotational movement of the rotary frame 7 and the translational movement of the bearing device. The effect is that the ratio between translational and rotational speeds is constant, it being possible to adjust this ratio by a desired value for the feed h of the bearing device being selected per rotation of the rotary frame.

It is therefore possible for a volume of an object to be examined, which is located on the bearing device 9, to be examined in the course of volume scanning. It is possible for the volume scanning to be performed in the form of spiral scanning with the effect that, with simultaneous rotation of the measuring unit 1 and translation of the bearing device 9, a large number of projections from various projection directions is recorded by way of the measuring unit per revolution of the measuring unit 1. During the spiral scanning, the focus F of the X-ray source is moved relative to the bearing device 9 on a spiral path designated by S in FIG. 1.

However, because there is a plurality of rows of detector elements 4, a volume of the object to be examined can also be examined in the course of so-called tomogram scanning in which there is no relative movement in the direction of the z axis between measuring unit 1 and bearing device 9. In the case of tomogram scanning, therefore, the size of the volume examined is determined by the number of active rows of detector elements 4.

During tomogram scanning, the focus F moves on a circular focal path which lies in a plane designated the central plane below. The straight line of intersection of the central plane with the plane of the drawing is indicated by dashes in FIG. 2 and designated by MP, the central plane being at right angles to the plane of the drawing in FIG. 2. A segment of the circular focal path is indicated by dots in FIG. 1 and designated by CP.

The tomogram scanning can be carried out in the form of a partial revolution or in the form of a complete revolution, the partial revolution covering a partial revolution interval of at least $\pi+\phi$, which permits complete reconstruction of a CT image, while a full revolution covers $2\pi$.

The measured data read out in parallel from the detector elements of each active row of the detector system 5 during the spiral or tomogram scanning and corresponding to the individual projections are subjected to digital/analog conversion in a data conditioning unit 10, are serialized and transmitted to an image computer 11.

After the measured data have been preprocessed in a preprocessing unit 12 belonging to the image computer 11, the resulting data stream passes to a slice reconstruction unit 13, which uses the measured data to reconstruct slices of desired layers of the object to be examined. In the case of spiral scanning, this is performed using a method known per se (for example 180LI or 360LI interpolation), and, in the case of tomogram scanning, using a method according to an embodiment of the invention that is yet to be explained in detail.

The CT images are composed of pixels assembled in the form of a matrix, the pixels being associated with the respective image plane, each pixel being assigned a CT number in Hounsfield units (HU) and the individual pixels being displayed in accordance with a CT index/gray value scale with a gray value corresponding to their respective CT number.

The images reconstructed by the slice reconstruction unit 13 and the shadowgram reconstruction unit 15 are displayed on a display unit 16, for example a monitor, connected to the image computer 11.

The X-ray source 2, for example an X-ray tube, is supplied by a generator unit 17 with the requisite voltages and currents, for example the tube voltage U. In order to be able to set the latter to the respectively requisite values, the generator unit 17 is assigned a control unit 18 with a keyboard 19, which permits the values to be set as required.

In addition, the operation and control of the CT device apart from this is carried out by way of the control unit 18 and the keyboard 19, which is illustrated by the fact that the control unit 18 is connected to the image computer 11.

Amongst other things, the number N of the active rows of detector elements 4, and therefore the position of the radiation apertures 3 and 6, can be set, for which purpose the control unit 18 is connected to the adjustment units 20 and 21 assigned to the radiation apertures 3 and 6. In addition, the rotation time $\tau$ can be set, which is the time needed by the rotary frame 7 for a complete revolution and which is illustrated by the fact that the drive unit 22 associated with the rotary frame 7 is connected to the control unit 18.

In the case where tomogram scanning is carried out, the calculation of the corresponding CT images is performed using a method according to the invention that is explained in more detail below.

In this case, in an operating mode corresponding to a first embodiment of the method according to an embodiment of the invention, tomogram scanning is carried out in the form of a full revolution ($2\pi$). Extracted from the measured data thereby obtained is a number of measured data corresponding to mutually overlapping partial revolution intervals $N_\alpha$, from which in each case a number of raw images $N_{tilt}$ are calculated, whose pixels relate to different image planes inclined with reference to the central plane.

Figure 3:
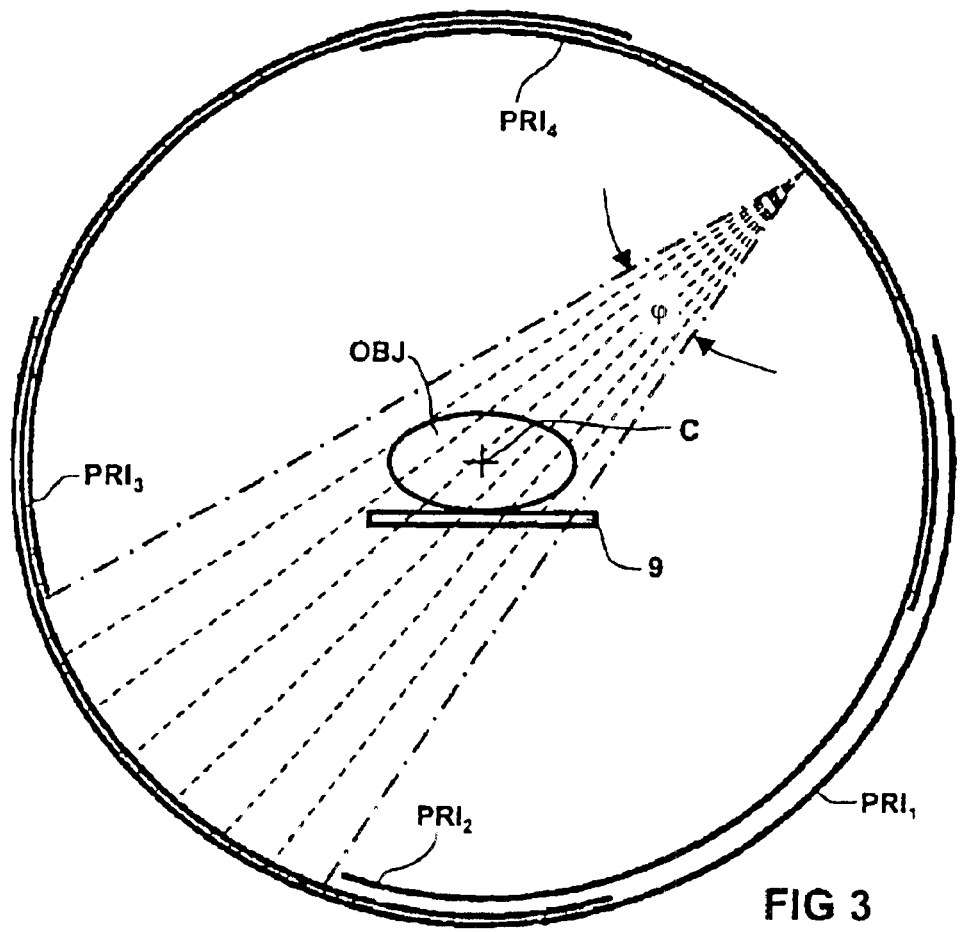
FIG. 3 shows a further operating mode of the CT device in accordance with FIGS. 1 and 2, in an illustration analogous to FIG. 2.

It may be seen from FIG. 3, in which an object to be examined, illustrated in cross section, is designated by OBJ, that, in the case of the exemplary embodiment described, there are four mutually overlapping partial revolution intervals, that is to say it holds that $N_\alpha=4$. The partial revolution intervals are designated in FIG. 3 by $PRI_1$ to $PRI_4$. In order to form a partial revolution interval, it may be necessary to bring together measured data from the start and end of the tomogram scanning to form a partial revolution interval.

Figure 4:
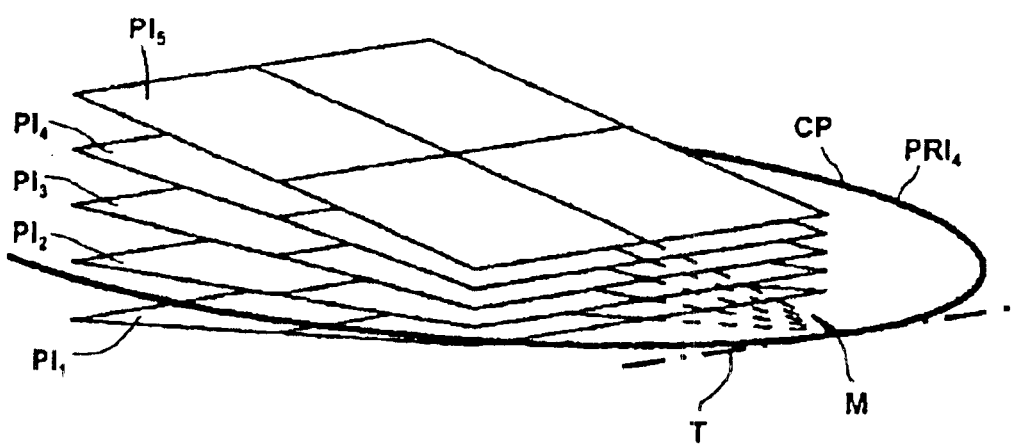
FIG. 4 shows a further CT device in an operating mode with a greater number of active rows of detector elements than in FIGS. 2 and 3, in an illustration analogous to FIG. 2.

As may be seen from FIG. 4, using the example of the partial revolution interval $PRI_4$, five raw images are calculated per partial revolution interval in the case of the exemplary embodiment described, that is to say it holds that $N_{tilt}=5$, which is illustrated by the image planes $PI_1$ to $PI_5$ of the raw images. Thus, a total of $N_\alpha * N_{tilt}$ 20 raw images are calculated from the measured data of the full revolution, and are finally combined to form a resulting CT image.

The image planes $PI_1$ to $PI_5$ Of the raw images all intersect in a straight line in accordance with FIG. 4. In the case of the exemplary embodiment illustrated, this straight line is the tangent T at the center M of the respective partial revolution, that is to say at that point of the segment, belonging to the partial revolution interval, of the focal path that is situated at half the arc length of this segment of the focal path.

For each of these image planes $PI_1$ to $PI_5$, those measured values that correspond to the line integrals required for a complete reconstruction of the respective raw image are now selected from the measured data supplied from the various detector rows $L_1$ to $L_8$. The selection is performed in such a way that the rays used for the reconstruction of the respective raw image fulfil a suitable error criterion with regard to their distance from the inclined image plane of the respective raw image. This is, in the case of the exemplary embodiment described, the minimum quadratic mean value of the distance, measured in the z direction, of all the rays. This is used for the reconstruction of the respective raw image, from the respective inclined image plane $PI_1$ to $PI_5$.

The maximum inclination of a preliminary image plan e is therefore determined by the requirement that there must be available for all the requisite line integrals measured values whose rays are situated satisfactorily close to the inclined image plane in accordance with the error criterion.

These line integrals assembled from various measured values for each image planes $PI_1$ to $PI_5$ are now used to calculate a raw image belonging to the respective image plane $PI_1$, to $PI_5$, for example by way of the standard reconstruction method of convolution and back projection.

The pixels of this raw image belong to the respective inclined image plane $PI_1$ to $PI_5$. Thus, a stack of five raw images is calculated for each partial revolution interval in the case of the exemplary embodiment described.

The $N_\alpha * N_{tilt}$ raw images thus obtained are combined in a subsequent reformatting step to form a resulting CT image of a desired image plane that differs from the image planes $PI_1$, to $PI_5$, specifically as a function of selectable submodes yet to be explained, either by weighting or by interpolation. Independently of the respective submode, the image noise is reduced in the, course of the combination, and the desired reconstruction layer thickness is set.

In an operating mode corresponding to a second embodiment of the method according to an embodiment of the invention, instead of being calculated from measured data of a plurality of partial revolution intervals obtained in the course of a full revolution, the raw images are calculated only from measured data of a single partial revolution interval. This operating mode is advantageous, in particular, for applications in which the aim is to achieve as high a temporal resolution as possible, for example examinations of the heart.

Whereas in the case of the first operating mode the raw images belonging to a plurality of partial revolution intervals are combined to form a resulting CT image, it follows that in the case of the second operating mode only raw images belonging to a single partial revolution interval are combined to form a resulting CT image.

The combination of raw images to form a resulting CT image is performed according to a first submode, selectable both in the first and in the second operating mode, by weighting. The procedure is such in the case of the combination by weighting that it is performed according to one of two selectable weighting modes in a fashion independent of the respectively selected weighting mode in such a way that the pixels of the raw images in each case contribute as source pixels to a corresponding target pixel of the resulting CT image. Further, the contribution of a source pixel to a target pixel is weighted as a function of a geometric reference variable. In other words: the CT number belonging to a target pixel is respectively determined from the CT numbers of the corresponding source pixels taking account of the geometric reference variable.

In the first weighting mode, the distance of the respective source pixel from the corresponding target pixel is taken into account as a geometric reference variable.

In the second weighting mode, in order to avoid artifacts an additional weighting is performed as a function of the distance of the source pixels from the center of the respective partial revolution interval.

In a second submode, the combination of the raw images to form a resulting CT image is performed by interpolation, that is to say the target pixels, i.e. the pixels of the resulting CT image, are determined by interpolation, for example linear interpolation, from corresponding pixels of the raw images.

Apart from the described operating modes, submodes and weighting modes, it is possible to select so-called slice modes that determine those image planes for which the resulting CT image is generated.

Apart from a first slice mode in which the resulting CT image is determined for an image plane at right angles to the system axis, for example the central plane MP, a second slice mode is provided in which the resulting CT image is determined for an image plane inclined with reference to the system axis, for example the image plane NP in accordance with FIG. 3. For the first slice mode, it is possible to use the keyboard to input the z position of the image plane, that is to say the point of intersection of the image plane with the system axis Z. For the second slice mode, it is, possible, in addition, to use the keyboard to input the angle of inclination of the image plane with reference to two axes of the three-dimensional coordinate system illustrated in FIG. 1.

It is possible in a third slice mode, for example by using a light pen 24 to draw on the monitor 16, to provide a curved section, for example the curved section CA in accordance with FIG. 1, for which the resulting CT image is determined. The point of intersection of the curved section CA with the system axis Z can be marked by use of the light pen 24, and the z position curved section CA on the system axis Z can be input via the keyboard 19.

The spatial position of the respectively selected image plane and, in the case of a section, also the course thereof are taken into account when combining the raw images to form a resulting CT image, by virtue of the fact that, depending on the selected submode, arbitrary oblique or even curved secondary sections are also produced directly from the stack of preliminary images (if appropriate, also from a plurality of stacks of different adjacent tomograms) in the weighting or interpolation method.

If no suitable measured values, that is to say rays, are available for fulfilling the error criterion, measured values corresponding to the error criterion can be obtained from a plurality of measured values situated near the image plane of the raw image, but not sufficiently near according to the error criterion, for example by adding up said measured values in conjunction with suitable weighting.

The method according to an embodiment of the invention also includes the possibility of forming a resulting CT image by superimposing raw images of a plurality of stacks of raw images that have been obtained on the basis of tomogram scannings with various central planes spaced apart preferably only slightly in the z direction.

In the case of the exemplary embodiments described, the relative movement between the measuring unit 1 and bearing device 9 is in each case produced by the bearing device 9 being displaced. However, within the scope of an embodiment of the invention, there is also the possibility of leaving the bearing device 9 in a fixed position, and instead, of displacing the measuring unit 1. In addition, within the scope of an embodiment of the invention, there is the possibility of producing the necessary relative movement by displacing both the measuring unit 1 and the bearing device 9.

The conical X-ray beam has a rectangular cross section in the case of the exemplary embodiment described. However, other cross-sectional geometries are also possible within the scope of the embodiments of the invention.

In connection with the exemplary embodiments described above, CT devices of the third generation are used, that is to say the X-ray source and the detector system are displaced jointly about the system axis during the image production. However, the embodiments of the invention can also be used in conjunction with CT devices of the fourth generation, in which only the X-ray source is displaced about the system axis and interacts with a stationary detector ring, if the detector system is a multi-row array of detector elements.

The method according to an embodiment of the invention can also be used in CT devices of the fifth generation, that is to say CT devices in which the X-radiation does not emanate from only one focus but from a plurality of foci of one or more X-ray sources displaced about the system axis, if the detector system has a multi-row array of detector elements.

The CT devices used in conjunction with the exemplary embodiments described above have a detector system with detector elements arranged in the manner of an orthogonal matrix. However, embodiments of the invention can also be used in conjunction with CT devices whose detector system has detector elements arranged in a two-dimensional array in another manner.

The exemplary embodiments described above relate to the medical application of the method according to embodiments of the invention. However, embodiments of the invention can also be applied outside medicine, for example in luggage checking or in material examination.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for computed tomography, comprising:
   scanning an object with the aid of a conical beam emanating from a focus and with the aid of a detector system, including a plurality of rows of detector elements for detecting the beam, by moving the focus on a focal path about a system axis without relative movement between the object and the focus in the direction of the system axis;
   supplying measured data corresponding to the received radiation via the detector system, wherein the length of the focal path is at least equal to the length of a partial revolution interval whose length suffices for the complete reconstruction of a CT image;
   calculating raw images, whose image planes are inclined relative to a central plane containing the focal path, from the measured data originating from a partial revolution interval; and
   combining a plurality of raw images to form a resulting CT image.

2. The method as claimed in claim 1, wherein the raw images are combined by weighting, the pixels of the raw images in each case contributing as source pixels to a corresponding target pixel of the resulting CT image, and wherein the contribution of a source pixel to a target pixel is weighted as a function of a geometric reference variable.

3. The method as claimed in claim 2, wherein the distance of the respective source pixel from the center of the corresponding partial revolution interval is taken into account as a geometric reference variable.

4. The method as claimed in claim 2, wherein the distance of the respective source pixel from the corresponding target pixel is taken into account as a geometric reference variable.

5. The method as claimed in claim 4, wherein the distance of the respective source pixel from the center of the corresponding partial revolution interval is taken into account as a geometric reference variable.

6. The method as claimed in claim 2, wherein raw images are calculated with reference to a plurality of partial revolution intervals, and wherein raw images originating from different partial revolution intervals are superimposed to form the resulting CT image.

7. The method as claimed in claim 6, wherein raw images are calculated with reference to a plurality of mutually overlapping partial revolution intervals.

8. The method as claimed in claim 2, wherein measured data are obtained that, for each row of detector elements, include one ray per position of the focus and per detector element, and wherein reconstruction of a raw image is performed on the basis of measured data that are selected from the measured data, supplied from the individual rows of detector elements, in such a way that the rays used for the reconstruction of the respective raw image fulfill an error criterion with regard to their distance from the inclined image plane of the respective raw image.

9. The method as claimed in claim 8, wherein the minimum quadratic mean value of the distance, measured in the z direction, of all the rays, used for the reconstruction of the respective raw image, from the inclined image plane of the respective raw image is provided as an error criterion.

10. The method as claimed in claim 1, wherein the combination of the raw images is performed by interpolation.

11. The method as claimed in claim 1, wherein raw images are calculated whose image planes intersect in a straight line.

12. The method as claimed in claim 11, wherein the image planes of the raw images intersect at a tangent to the focal path.

13. The method as claimed in claim 1, wherein raw images are calculated with reference to a plurality of partial revolution intervals, and wherein raw images originating from different partial revolution intervals are superimposed to form the resulting CT image.

14. The method as claimed in claim 13, wherein raw images are calculated with reference to a plurality of mutually overlapping partial revolution intervals.

15. The method as claimed in claim 1, wherein measured data are obtained that, for each row of detector elements, include one ray per position of the focus and per detector element, and wherein reconstruction of a raw image is performed on the basis of measured data that are selected from the measured data, supplied from the individual rows of detector elements, in such a way that the rays used for the reconstruction of the respective raw image fulfill an error criterion with regard to their distance from the inclined image plane of the respective raw image.

16. The method as claimed in claim 15, wherein the minimum quadratic mean value of the distance, measured in the z direction, of all the rays, used for the reconstruction of the respective raw image, from the inclined image plane of the respective raw image is provided as an error criterion.

17. The method as claimed in claim 1, wherein the layer thickness of the resulting CT image is set via the number of raw images incorporated into the combination.

18. The method as claimed in claim 1, wherein the layer thickness of the resulting CT image is set by weighting the raw images incorporated into the combination.

19. The method as claimed in claim 1, wherein a raw image whose image plane is the central plane is calculated and incorporated into the combination.

20. The method as claimed in claim 1, wherein an axial image is produced as the resulting CT image.

21. The method as claimed in claim 1, wherein a resulting CT image with an image plane inclined with respect to the central plane is produced.

22. The method as claimed in claim 1, wherein the calculation of the raw images is performed by image reconstruction.

23. The method as claimed in claim 1, wherein the calculation of the raw images is performed by image reconstruction on the basis of a conventional reconstruction method.

24. An apparatus for performing the method of claim 1.

25. A computed tomography device, comprising:
- a radiation source with a focus from which a conical beam serving for scanning an object emanates;
- a detector system, including a plurality of rows of detector elements, for detecting the beam, wherein the focus is moved on a focal path about a system axis, without a relative movement taking place between the object and the focus in the direction of the system axis, wherein the detector system is adapted to supply measured data corresponding to the received radiation, and wherein the length of the focal path is at least equal to the length of a partial revolution interval whose length suffices for the complete reconstruction of a CT image;
- an image computer, adapted to use measured data originating from a partial revolution interval to calculate raw images whose image planes are inclined relative to a central plane containing the focal path, and adapted to combine a plurality of raw images to form a resulting CT image.

26. The CT device as claimed in claim 25, wherein the image computer undertakes the combination of the raw images by weighting, the pixels of the raw images in each case contributing as source pixels to a corresponding target pixel of the resulting CT image, and wherein the contribution of a source pixel to a target pixel is weighted as a function of a geometric reference variable.

27. The CT device as claimed in claim 26, wherein the image computer is adapted to take account of the distance of the respective source pixel from the center of the corresponding partial revolution interval as a geometric reference variable.

28. The CT device as claimed in claim 26, wherein the image computer takes account of the distance of the respective source pixel from the corresponding target pixel as a geometric reference variable.

29. The CT device as claimed in claim 28, wherein the image computer takes account of the distance of the respective source pixel from the center of the corresponding partial revolution interval as a geometric reference variable.

30. The CT device as claimed in claim 25, wherein the image computer is adapted to undertake the combination of the raw images by interpolation.

31. The CT device as claimed in claim 25, wherein the image computer is adapted to calculate raw images whose image planes intersect in a straight line.

32. The CT device as claimed in claim 31, wherein the image planes of the raw images intersect at a tangent to the focal path.

33. The CT device as claimed in claim 25, wherein the image computer is adapted to calculate raw images with reference to a plurality of partial revolution intervals, and is adapted to superimpose raw images originating from different partial revolution intervals to form the resulting CT image.

34. The CT device as claimed in claim 33, wherein the image computer is adapted to calculate raw images with reference to a plurality of mutually overlapping partial revolution intervals.

35. The CT device as claimed in claim 25, wherein the detector system is adapted to obtains measured data that, for each row of detector elements, include one ray per position of the focus and per detector element, and wherein the image computer is adapted to undertakes the reconstruction of a raw image on the basis of measured data which it selects from the measured data, supplied from the individual rows of detector elements, in such a way that the rays used for the reconstruction of the respective raw image fulfill an error criterion with regard to their distance from the inclined image plane of the respective raw image.

36. The CT device as claimed in claim 35, wherein the image computer is adapted to use the minimum quadratic mean value of the distance, measured in the z direction, of all the rays, used for the reconstruction of the respective raw image, from the inclined image plane of the respective raw image as an error criterion.

37. The CT device as claimed in claim 25, wherein the layer thickness of the resulting CT image is adapted to be set via the number of raw images incorporated into the combination.

38. The CT device as claimed in claim 25, wherein the layer thickness of the resulting CT image is adapted to be set by weighting the raw images incorporated into the combination.

39. The CT device as claimed in claim 25, wherein the image computer is adapted to calculate a raw image whose image plane is the central plane, and incorporates it into the combination.

40. The CT device as claimed in claim 25, wherein the image computer is adapted to produce an axial image as the resulting CT image.

41. The CT device as claimed in claim 25, wherein a resulting CT image with an image plane inclined with reference to the central plane is produced.

42. The CT device as claimed in claim 25, wherein the image computer is adapted to undertakes the calculation of the raw images by image reconstruction.

43. The CT device as claimed in claim 25, wherein the image computer is adapted to undertake the calculation of the raw images by image reconstruction on the basis of a conventional reconstruction method.

44. A method for computed tomography, comprising:
- moving a focus of a conical beam over an object, wherein the focus is moved on a focal path about an axis without relative movement between the object and the focus in the direction of the axis;
- measuring data for the object based upon radiation received by a detector system, including a plurality of rows of detector elements for detecting the beam, to scan wherein the length of the focal path is at least equal to the length of a partial revolution interval whose length suffices for the complete reconstruction of a CT image;
- calculating raw images, with image planes inclined relative to a central plane containing the focal path, from the measured data originating from a partial revolution interval; and
- combining a plurality of raw images to form a CT image.

45. An apparatus for performing the method of claim 44.

46. A computed tomography apparatus, comprising:
- means for moving a focus of a conical beam over an object, wherein the focus is moved on a focal path about an axis without relative movement between the object and the focus in the direction of the axis;
- means for measuring data for the object based upon radiation received by a detector system, including a plurality of rows of detector elements for detecting the beam, to scan wherein the length of the focal path is at least equal to the length of a partial revolution interval whose length suffices for the complete reconstruction of a CT image;
- means for calculating raw images, with image planes inclined relative to a central plane containing the focal path, from the measured data originating from a partial revolution interval; and means for combining a plurality of raw images to form a CT image.

47. A computed tomography device, comprising:

means for scanning an object using a radiation source with a focus from which a conical beam emanates;

means for detecting the beam to produced measured data, wherein the focus is moved without relative movement taking place between the object and the focus in the direction of a system axis; and means for producing raw images from the measured data originating from a partial revolution interval, whose image planes are inclined relative to a central plane containing the focal path, and for combining a plurality of raw images to form a resulting CT image.

* * * * *